United States Patent
Linder

(10) Patent No.: US 9,205,044 B2
(45) Date of Patent: Dec. 8, 2015

(54) AQUEOUS PHARMACEUTICAL PREPARATION COMPRISING ROFLUMILAST

(75) Inventor: Rudolf Linder, Constance (DE)

(73) Assignee: TAKEDA GMBH, Constance (DE)

( * ) Notice: Subject to any disclaimer, the term of this patent is extended or adjusted under 35 U.S.C. 154(b) by 2603 days.

(21) Appl. No.: 11/662,887

(22) PCT Filed: Sep. 21, 2005

(86) PCT No.: PCT/EP2005/054723
§ 371 (c)(1),
(2), (4) Date: Mar. 15, 2007

(87) PCT Pub. No.: WO2006/032675
PCT Pub. Date: Mar. 30, 2006

(65) Prior Publication Data
US 2007/0259009 A1    Nov. 8, 2007

(30) Foreign Application Priority Data

Sep. 22, 2004 (DE) .......... 10 2004 046 235

(51) Int. Cl.
| | |
|---|---|
| *A61K 9/08* | (2006.01) |
| *A61K 9/00* | (2006.01) |
| *A61K 31/44* | (2006.01) |
| *A61K 47/10* | (2006.01) |
| *A61K 47/12* | (2006.01) |
| *A61K 47/14* | (2006.01) |

(52) U.S. Cl.
CPC ............... *A61K 9/0019* (2013.01); *A61K 9/08* (2013.01); *A61K 31/44* (2013.01); *A61K 9/0043* (2013.01); *A61K 9/0048* (2013.01); *A61K 47/10* (2013.01); *A61K 47/12* (2013.01); *A61K 47/14* (2013.01)

(58) Field of Classification Search
None
See application file for complete search history.

(56) References Cited

U.S. PATENT DOCUMENTS

| | | |
|---|---|---|
| 6,630,161 B1 * | 10/2003 | Leesman ............ 424/455 |
| 2002/0193393 A1 | 12/2002 | Pairet et al. |
| 2004/0058950 A1 | 3/2004 | Meade et al. |
| 2004/0151722 A1 * | 8/2004 | Banerjee et al. ....... 424/145.1 |

FOREIGN PATENT DOCUMENTS

| | | |
|---|---|---|
| WO | 95/01338 | 1/1995 |
| WO | 00/53182 A3 | 9/2000 |
| WO | WO 03070279 A1 * | 8/2003 |
| WO | 03/099334 | 12/2003 |
| WO | 03/105902 | 12/2003 |
| WO | WO 03099278 A1 * | 12/2003 |

OTHER PUBLICATIONS

SOLUTOL® HS 15 Technical Information, Jul. 2003.*
Defintion of "solution, colloidal" from Hawley's Chemical Condensed Dictionary, 14th edition, 2002.*
R. Strickley, "Solubilizing Excipients in Oral and Injectable Formulations." *Pharmaceutical Research*, v.21:2, pp. 201-230, 2004.
Adis International Ltd, "(Abs.) Roflumilast: APTA 2217, B9302-107, BY 217, BYK 20869." *Drugs in R&D*, v.5:3, pp. 176-181(6), 2004.
Kumar et al., "Inhibition of Inflammation and Remodeling by Roflumilast and Dexamethasone in Murine Chronic Asthma." *The Journal of Pharmacology and Experimental Theraputics*, v.307, pp. 349-355, 2003.

* cited by examiner

*Primary Examiner* — Nissa Westerberg
(74) *Attorney, Agent, or Firm* — Nath, Goldberg & Meyer; Joshua B. Goldberg; Scott H. Blackman

(57) ABSTRACT

An aqueous pharmaceutical preparation for administration of a slightly soluble PDE4 inhibitor is described.

2 Claims, No Drawings

AQUEOUS PHARMACEUTICAL PREPARATION COMPRISING ROFLUMILAST

This application was filed under 35 U.S.C. 371 as a national stage of PCT/EP2005/054723, filed Sep. 21, 2005.

TECHNICAL FIELD

The present invention relates to the field of pharmaceutical technology and describes an aqueous pharmaceutical preparation comprising a slightly soluble PDE 4 inhibitor as active ingredient. The invention further relates also to processes for producing the pharmaceutical preparation and to the use of the pharmaceutical preparation for the treatment of disorders.

PRIOR ART

Cyclic nucleotide phosphodiesterase (PDE) inhibitors (in particular of type 4) are currently of particular interest as a new generation of active ingredients for the treatment of inflammatory disorders, especially disorders of the respiratory tract such as asthma or airway obstructions (such as, for example, COPD=chronic obstructive pulmonary disease). A number of PDE 4 inhibitors is currently undergoing advanced clinical trials, including a dosage form for oral administration comprising the active ingredient N-(3,5-dichloropyrid-4-yl)-3-cyclopropylmethoxy-4-difluoromethoxybenzamide (INN: roflumilast). This and other compounds having a benzamide structure and their use as cyclic nucleotide phosphodiesterase (PDE) inhibitors are described in WO95/01338. These active ingredients are proposed in WO95/01338 also for the treatment of certain disorders of the skin (such as, for example, dermatoses). WO00/53182 proposes the use of roflumilast or its N-oxide for the treatment of multiple sclerosis. WO03/099334 describes pharmaceutical preparations for slightly soluble PDE 4 inhibitors such as, for example, ointments and aqueous or oily suspensions and emulsions.

Besides oral dosage forms, it may also be necessary and advantageous to provide an active ingredient as parenteral form (preparation intended for injection), especially for groups of patients who have problems with taking oral dosage forms.

Parenteral preparations must be produced with particular care in order to guarantee freedom from irritation and to avoid microbial and particulate contaminants. The most important solvent or dispersant is water. According to the pharmacopeia, water for injections must always be used in these cases. Active ingredients to be administered intravenously must be completely dissolved. It must furthermore be ensured during development of the preparation that no precipitation takes place during the injection. Further requirements to be mentioned for parenteral preparations are in particular good tolerability for the patient. This may depend on the aqueous preparation being rendered isotonic or approximately isotonic and having an approximately physiological pH, and on the absence of particulate contaminants.

The production of parenteral preparations or of general solutions of active ingredients which are slightly soluble in water therefore involves particular problems. For example, for the PDE 4 inhibitor N-(3,5-dichloropyrid-4-yl)-3-cyclopropylmethoxy-4-difluoromethoxybenzamide (INN: roflumilast) described in WO95/01338 the solubility in water is observed to be only 0.53 mg/l at 21° C. Replacement of water by other solvents or the use of solubilizers [e.g. solubilizers such as lecithin and poloxamer 188 (Pluronic F68®)] is, however, possible to only a limited extent for producing parenteral preparations or solutions for other purposes for the reasons indicated above. An attempt to produce an aqueous solution of roflumilast, e.g. for injection, does not, despite addition of the solubilizer poloxamer 188 which is normally employed in connection with parenteral preparations, result in a solution having a roflumilast concentration which is acceptable for injections.

DESCRIPTION OF THE INVENTION

It has now been found, surprisingly, that roflumilast can be dissolved in water in an amount which is sufficient for injections when alkoxylated fats are used as cosolvent. It is possible on this basis to obtain clear solutions having the properties necessary for parenteral preparations (in particular good tolerability for the patient, no particulate contaminants). In particular, the solution is also stable during storage and no precipitates of the active ingredient are observed. Furthermore, compatibility with the container material is good.

The invention therefore relates to an aqueous pharmaceutical preparation comprising an active ingredient in a therapeutically effective and pharmacologically acceptable amount and alkoxylated fat, where the active ingredient is selected from the group consisting of roflumilast, salts of roflumilast, the N-oxide of the pyridine residue of roflumilast or salts thereof. The aqueous preparation is in particular a solution in which the active ingredient is completely dissolved.

Roflumilast is the INN for a compound of the formula I

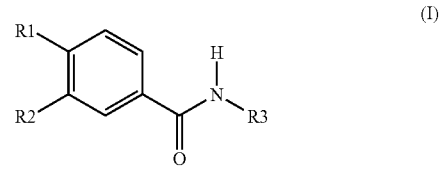

in which
R1 is difluoromethoxy,
R2 is cyclopropylmethoxy and
R3 is 3,5-dichloropyrid-4-yl.

This compound has the chemical name N-(3,5-dichloropyrid-4-yl)-3-cyclopropylmethoxy-4-difluoromethoxybenzamide (INN: roflumilast). The N-oxide of roflumilast has the chemical name 3-cyclopropylmethoxy-4-difluoromethoxy-N-(3,5-dichloropyrid-4-yl 1-oxide)benzamide.

This compound of the formula I, its salts, the N-oxide, its salts and the use of these compounds as phosphodiesterase (PDE) 4 inhibitors are described in the International Patent Application WO95/01338.

Salts suitable for compounds of the formula I—depending on the substitution—are all acid addition salts but, in particular, all salts with bases. Particular mention may be made of the pharmacologically acceptable salts of the inorganic and organic acids and bases normally used in pharmaceutical technology. Pharmacologically unacceptable salts which, for example, may be the initial products of the process for preparing the compounds of the invention on the industrial scale are converted into pharmacologically acceptable salts by processes known to the skilled worker. Those suitable on the one hand are water-soluble and water-insoluble acid addition salts with acids such as, for example, hydrochloric acid, hydrobromic acid, phosphoric acid, nitric acid, sulphuric acid, acetic acid, citric acid, D-gluconic acid, benzoic acid, 2-(4-hydroxybenzoyl)benzoic acid, butyric acid, sulphosalicylic acid, maleic acid, lauric acid, malic acid, fumaric acid, succinic acid, oxalic acid, tartaric acid, embonic acid, stearic acid, toluenesulphonic acid, methanesulphonic acid, or 3-hydroxy-2-naphthoic acid, the acids being employed to prepare the salts in the equimolar ratio of amounts, or one differing therefrom—depending on whether the acid is monobasic or polybasic and depending on which salt is desired.

On the other hand, salts with bases are also particularly suitable. Examples of basic salts which may be mentioned are lithium, sodium, potassium, calcium, magnesium, ammonium, meglumine or guanidinium salts, once again the bases being employed to prepare the salts in the equimolar ratio of amounts or one differing therefrom.

According to the invention, the alkoxylated fat is preferably a polyoxyethylated fatty acid, in particular polyoxyethylated 12-hydroxystearic acid. This is also referred to as macrogol 15-hydroxystearate or polyethylene glycol 15-hydroxystearate. Products based on this are obtainable, for example, from BASF under the designation Solutol® HS 15. Solutol® HS 15 consists of polyglycol mono- and diesters of 12-hydroxystearic acid and approximately 30% free polyethylene glycol, where parts of the 12-hydroxy group may also be etherified with polyethylene glycol (see Technical Information Solutol® HS 15 Nov. 2002; BASF). The alkoxylated fat is preferably present in a pharmaceutically acceptable amount in the dosage form according to the invention.

The preparation according to the invention is preferably a preparation based on water, particularly preferably water for injections.

The preparation according to the invention may if desired comprise further pharmaceutical excipients suitable for parenteral preparations. Examples which should be mentioned here are substances for improving the solubility (e.g. cosolvents and solubilizers), substances for rendering isotonic, buffers, antioxidants, chelating agents, preservatives, emulsifiers, bases or acids for setting a physiological pH or excipients for prolonging the effect.

Suitable cosolvents are in particular ethanol, glycerol, propylene glycol and polyethylene glycol or 1,3-butanediol. Preference is given in this connection to propylene glycol and polyethylene glycol (especially macrogol 300/400). Solubilizers which should be mentioned are lecithin and poloxamer 188 (Pluronic F68®), with preference for poloxamer 188.

Substances which are used for rendering isotonic and should be mentioned in particular are sodium chloride, glucose, mannitol, glycerol or else propylene glycol and polyethylene glycol.

Preservatives mentioned in particular are p-hydroxybenzoic esters, benzyl alcohol, phenylmercury salts or chlorocresol.

In a preferred embodiment, the preparation according to the invention comprises poloxamer 188 and/or polyethylene glycol as further pharmaceutical excipients.

100 ml of solution comprise from 0.001 to 0.1 parts by weight (gram), preferably from 0.005 to 0.09 gram of roflumilast, particularly preferably from 0.01 to 0.08 gram. Polyethylene glycol 15-hydroxystearate is employed in amounts of from 0.5 to 15 grams, preferably 1 to 12 grams, very particularly preferably 2 to 8 grams per 100 ml of solution. Poloxamer 188 is employed in amounts of from 0.01 to 5 grams, preferably 0.1 to 4 grams, very particularly preferably 0.2 to 4 grams per 100 ml of solution. The amount of polyethylene glycol 300 or 400 or propylene glycol is preferably from 3 to 15 grams per 100 ml of solution. The quantitative data are preferably data relating to solutions for injection.

The pharmaceutical preparation according to the invention can be produced by processes familiar to the skilled person.

The active ingredient is preferably dissolved in the alkoxylated fat, optionally with heating. The alkoxylated fat may if desired additionally contain poloxamer 188. By adding polyethylene glycol (macrogol 300/400) and/or propylene glycol, an improvement in the dissolution of the active ingredient can be achieved. At the same time polyethylene glycol (macrogol 300/400) and/or propylene glycol can also be employed to render the preparation isotonic. After adding water to the solution of the active ingredient in the alkoxylated fat a clear solution is obtained. The solution obtained in this way can then be sterilized by filtration and subsequently dispensed into suitable containers such as vials or ampoules. The solution can alternatively first be introduced into suitable containers, and this solution can then be subjected in the final container to a sterilization, for example by autoclaving. If the preparations according to the invention are dispensed in multidose containers a preservative is preferably added.

The following examples serve to illustrate the invention without restricting it.

Production of the Dosage Forms According to the Invention

EXAMPLE 1

4 grams of polyethylene glycol 400, 8 grams of Solutol HS15 and 2 g of poloxamer 188 are heated to give a clear melt. 0.04 gram of roflumilast is added, and the mixture is stirred until a clear solution is obtained. While stirring, water is slowly added to make up to 100 ml. If necessary, the pH of the solution is adjusted to 7.0 to 7.4 with a suitable base. The clear solution obtained in this way is sterilized by filtration and bottled under aseptic conditions. This solution can also be employed in eye drops or compositions for nasal administration.

EXAMPLE 2

2 grams of Solutol HS15 are heated to give a clear melt, and 4 milligrams of roflumilast are dissolved to give a clear solution therein. Physiological saline is used to make up to 100 ml. If necessary, the pH of the solution is adjusted to 7.0 to 7.4 with a suitable base. The clear solution obtained in this way is sterilized by filtration and can be dispensed into ampoules for parenteral administration or into single-use containers for use on the eye or in containers for use in the nose (eye drops in multidose containers require a preservative).

EXAMPLE 3

4 grams of polyethylene glycol 400 and 8 grams of Solutol HS15 are heated to give a clear solution, 0.02 g of roflumilast is added and, after dissolution is complete, water is used to make up slowly to 100 ml. If necessary, the pH of the solution is adjusted to 7.0 to 7.4 with a suitable base. The clear solution obtained in this way is sterilized by filtration and can then be dispensed into ampoules or containers for eye drops or containers for nasal administration.

Comparative Test-production of a Solution of Roflumilast Based on Water, Poloxamer 188 and Polyethylene Glycol

EXAMPLE 4

A clear solution is prepared (based on Example 1) from 4 grams of polyethylene glycol 400 and 2 grams of poloxamer 188. 0.04 g of roflumilast is added, and the mixture is stirred until a clear solution is obtained. While stirring, water is slowly added to make up to 100 ml. A bulky precipitate is formed.

EXAMPLE 5

A clear solution is prepared from 4 grams of polyethylene glycol 400 and 4 grams of poloxamer 188. 0.02 gram or 0.04 gram of roflumilast is added, and the mixture is stirred until a clear solution is obtained. While stirring, water is slowly added to make up to 100 ml. A bulky precipitate is formed in both cases.

EXAMPLE 6

A clear solution is prepared from 4 grams of polyethylene glycol 400 and 20 grams of poloxamer 188. 0.02 gram or 0.04 gram of roflumilast is added, and the mixture is stirred until a clear solution is obtained. While stirring, water is slowly added to make up to 100 ml. A bulky precipitate is formed in both cases.

INDUSTRIAL APPLICABILITY

The preparations of the invention can be employed for the treatment and prevention of all diseases regarded as treatable or preventable through the use of PDE 4 inhibitors. Selective cyclic nucleotide phosphodiesterase (PDE) inhibitors (specifically of type 4) are suitable on the one hand as bronchial therapeutic agents (for the treatment of airway obstructions owing to their dilating effect but also owing to their effect increasing the respiratory rate and respiratory drive) and for eliminating erectile dysfunction owing to the vasodilating effect, but on the other hand especially for the treatment of disorders, especially of an inflammatory nature, e.g. of the airways (asthma prophylaxis), of the skin, of the central nervous system, of the intestine, of the eyes and of the joints, which are promoted by mediators such as histamine, PAF (platelet-activating factor), arachidonic acid derivatives such as leukotrienes and prostaglandins, cytokines, interleukins, chemokines, alpha-, beta- and gamma-interferon, tumour necrosis factor (TNF) or oxygen free radicals and proteases. The pharmaceutical preparations of the invention can therefore be used in human and veterinary medicine for example for the treatment and prophylaxis of the following diseases: acute and chronic (especially inflammatory and allergen-induced) airway disorders of various aetiologies (bronchitis, allergic bronchitis, bronchial asthma, COPD); dermatoses (especially of a proliferative, inflammatory and allergic nature) such as, for example, psoriasis (vulgaris), toxic and allergic contact eczema, atopic eczema, seborrhoeic eczema, lichen simplex, sunburn, pruritus in the genitoanal region, alopecia areata, hypertrophic scars, discoid lupus erythematosus, follicular and extensive pyodermas, endogenous and exogenous acne, acne rosacea and other proliferative, inflammatory and allergic skin disorders; disorders based on excessive release of TNF and leukotrienes, e.g. disorders of the arthritic type (rheumatoid arthritis, rheumatoid spondylitis, osteoarthritis and other arthritic states), disorders of the immune system (AIDS, multiple sclerosis), types of shock [septic shock, endotoxin shock, Gram-negative sepsis, toxic shock syndrome and ARDS (adult respiratory distress syndrome)] and generalized inflammations in the gastrointestinal region (Crohn's disease and ulcerative colitis); disorders based on allergic and/or chronic abnormal immunological reactions in the region of the upper airways (pharyngeal space, nose) and adjacent regions (paranasal sinuses, eyes), such as, for example, allergic rhinitis/sinusitis, chronic rhinitis/sinusitis, allergic conjunctivitis, conjunctivitis caused by bacteria, viruses or fungi, inflammatory states after intraocular lens implantation, inflammation of the optic nerve (neuritis nervi optici), keratitis, dry eye syndrome (keratitis sicca), uveitis, glaucoma, retinal oedema, retinitis pigmentosa, diabetic retinopathy, and nasal polyps; but also cardiac disorders which can be treated by PDE inhibitors, such as, for example, heart failure, or disorders which can be treated owing to the tissue-relaxant effect of PDE inhibitors, such as, for example, erectile dysfunction or colic of the kidneys and ureters connected with kidney stones; or else disorders of the CNS such as, for example, depressions or arteriosclerotic dementia.

The pharmaceutical preparations of the invention are also suitable for the treatment of disorders of the skin such as dermatoses (especially of a proliferative, inflammatory and allergic nature) such as, for example, psoriasis (vulgaris), toxic and allergic contact eczema, atopic eczema, seborrhoeic eczema, lichen simplex, sunburn, pruritus in the genitoanal region, alopecia areata, hypertrophic scars, discoid lupus erythematosus, follicular and extensive pyodermas, endogenous and exogenous acne, acne rosacea and other proliferative, inflammatory and allergic skin disorders.

The preparations according to the invention in the form of a solution can be administered parenterally (e.g. as injection or infusion) or can also be administered topically, for example in the form of eye drops or as a nasal administration (for use on the nasal mucosa) for the treatment of the abovementioned diseases.

The invention further relates to a method for the treatment of mammals, including humans, suffering from one of the abovementioned diseases. The method is characterized in that a therapeutically effective and pharmacologically suitable amount of an active pharmaceutical ingredient selected from the group of compounds roflumilast, salts of roflumilast, the N-oxide of roflumilast and salts thereof is administered to the mammal with the disease, with the active pharmaceutical ingredient being administered in a pharmaceutical preparation of the invention. The method is characterized in that the administration takes place by parenteral administration (injection or infusion).

The invention further relates to a method for the treatment of mammals, including humans, suffering from one of the abovementioned diseases. The method is characterized in that a therapeutically effective and pharmacologically suitable amount of an active pharmaceutical ingredient selected from the group of compounds roflumilast, salts of roflumilast, the N-oxide of roflumilast and salts thereof is administered to the mammal with the disease, with the active pharmaceutical ingredient being administered in a pharmaceutical preparation of the invention. The method is characterized in that the administration takes place by nasal administration.

In another preferred embodiment, the invention relates to the treatment of mammals, including humans, suffering from an eye disorder which is regarded as treatable or preventable through use of PDE 4 inhibitors. The eye disorder is preferably selected from the group of allergic conjunctivitis, conjunctivitis caused by bacteria, viruses or fungi, inflammatory states after intraocular lens implantation, inflammation of the optic nerve (neuritis nervi optici), keratitis, dry eye syndrome (keratitis sicca), uveitis, glaucoma, retinal oedema, retinitis pigmentosa and diabetic retinopathy. The eye disorder is preferably allergic conjunctivitis, conjunctivitis caused by bacteria, viruses or fungi, inflammatory states after intraocular lens implantation or uveitis. The method is characterized in that the administration takes place by administration of the preparation according to the invention to the eye, especially in the form of eye drops.

The pharmaceutical preparations of the invention are moreover particularly suitable for administration to groups of patients who are suffering from the abovementioned diseases and have problems in taking pharmaceutical preparations to be administered orally, such as, for example, bedridden patients, patients in intensive medical care, patients with swallowing difficulties and children.

The invention further relates to a method for the treatment of mammals, including humans, suffering from one of the abovementioned diseases. The method is characterized in that a therapeutically effective and pharmacologically suitable amount of an active pharmaceutical ingredient selected from the group of compounds roflumilast, salts of roflumilast, the N-oxide of roflumilast and salts thereof is administered to the mammal with the disease, with the active pharmaceutical ingredient being administered in a topical pharmaceutical preparation of the invention.

The disease is preferably acute and chronic (especially inflammatory and allergen-induced) airway disorders of various aetiologies (bronchitis, allergic bronchitis, bronchial asthma, COPD), and disorders of the arthritic type (rheumatoid arthritis, rheumatoid spondylitis, osteoarthritis and other arthritic states).

The dosage forms of the invention comprise the active pharmaceutical ingredient in the dose customary for the treatment of the particular disease. The dosage of the active ingredient is of the order of magnitude customary for PDE inhibitors, it being possible to administer the daily dose in one or more dosage units. Customary dosages are disclosed for example in WO 95/01338. The normal dose on systemic therapy (oral) is between 0.001 and 3 mg per kilogram and day. Dosage forms preferred according to the invention for parenteral administration contain from 0.005 mg to 5 mg of roflumilast, preferably from 0.01 mg to 2.5 mg, particularly preferably 0.1 mg to 0.5 mg of roflumilast per dosage unit. Examples of pharmaceutical preparations of the invention contain 0.01 mg, 0.1 mg, 0.125 mg, 0.25 mg and 0.5 mg of roflumilast per dosage unit.

The invention claimed is:

1. An aqueous pharmaceutical preparation, which is a clear solution, comprising an active ingredient in a therapeutically effective and pharmacologically acceptable amount and alkoxylated fat, where the active ingredient is selected from the group consisting of roflumilast, salts of roflumilast, the N-oxide of the pyridine residue of roflumilast or salts thereof and poloxamer 188.

2. A process for producing a pharmaceutical preparation according to claim 1, comprising the steps of (a) dissolving the active ingredient in the alkoxylated fat and adding one or more substances selected from the group consisting of poloxamer 188, polyethylene glycol and propylene glycol preparations; and (b) adding water.

* * * * *